(12) United States Patent
Minagawa et al.

(10) Patent No.: US 8,333,719 B2
(45) Date of Patent: Dec. 18, 2012

(54) LOAD APPARATUS

(75) Inventors: Eiichi Minagawa, Mitaka (JP); Ryoichi Sakai, Mitaka (JP); Koji Ogawa, Mitaka (JP)

(73) Assignee: Hitachi Aloka Medical, Ltd., Tokyo (JP)

( * ) Notice: Subject to any disclaimer, the term of this patent is extended or adjusted under 35 U.S.C. 154(b) by 1297 days.

(21) Appl. No.: 12/059,246

(22) Filed: Mar. 31, 2008

(65) Prior Publication Data
US 2008/0242970 A1 Oct. 2, 2008

(30) Foreign Application Priority Data
Mar. 29, 2007 (JP) .................................. 2007-88150

(51) Int. Cl.
*A61B 5/103* (2006.01)
*A61B 5/117* (2006.01)
*A61B 5/00* (2006.01)
*A61B 19/00* (2006.01)
*B23Q 17/20* (2006.01)
*G01N 3/00* (2006.01)
*G01N 3/48* (2006.01)
*G01N 3/42* (2006.01)

(52) U.S. Cl. ............ 600/587; 600/552; 600/553; 73/78; 73/81; 73/82; 73/573; 73/574

(58) Field of Classification Search ................... 600/552, 600/553, 587; 607/51, 52; 73/78, 81–83, 73/573, 574, 862
See application file for complete search history.

(56) References Cited

U.S. PATENT DOCUMENTS
4,217,912 A * 8/1980 Hubmann et al. ............ 600/587
4,799,498 A 1/1989 Collier FOREIGN PATENT DOCUMENTS
| EP | 1 707 124 A2 | 4/2006 |
| FR | 2533030 | 3/1984 |
| JP | 54-50173 A | 4/1979 |
| JP | 04204249 | 7/1992 |

(Continued)

OTHER PUBLICATIONS

European Search Report dated Jul. 16, 2008; Application No. 08005619.5-2319.

(Continued)

*Primary Examiner* — Jeffrey G Hoekstra
*Assistant Examiner* — Devin Henson
(74) *Attorney, Agent, or Firm* — Westerman, Hattori, Daniels & Adrian, LLP

(57) ABSTRACT

An oscillation arm moves in a seesaw fashion about an oscillation axis which is supported by a support rod and which serves as a fulcrum. A rotation arm and a pressurizer are provided on one end of the oscillation arm. One end of the rotation arm is rotatably attached to the oscillation arm, and a load weight is placed on the other end of the rotation arm. By rotating the rotation arm, the magnitude of a force to be applied by the load weight to the pressurizer is adjusted. More specifically, by displacing the load weight to a predetermined position by rotation and then causing the load weight to stop at this position, a static load corresponding to the rotation angle can be applied to the pressurizer. Further, by causing the load weight to perform rotational motion, the magnitude of the force to be applied to the pressurizer is periodically varied, so that a load which varies periodically can be applied to hard tissue.

13 Claims, 7 Drawing Sheets

FOREIGN PATENT DOCUMENTS

| | | |
|---|---|---|
| JP | 7-43282 A | 2/1995 |
| JP | 8/245857 A | 9/1996 |
| JP | 2001-232290 A | 8/2001 |
| JP | 2003-270112 A | 9/2003 |
| JP | 2005-37262 A | 2/2005 |
| JP | 2005-152079 A | 6/2005 |
| JP | 2007-307042 A | 11/2007 |
| WO | 96/28510 A1 | 9/1996 |

OTHER PUBLICATIONS

Japanese Office Action dated Apr. 28, 2009 (mailing date), issued in corresponding Japanese Patent Application No. 2007-088150.

* cited by examiner

LOAD APPARATUS

BACKGROUND

1. Technical Field

The present invention relates to a load apparatus which applies a load to hard tissue such as a bone.

2. Related Art

Simple quantitative measurement of mechanical characteristics such as bone strength is desired for diagnosing bone metabolic diseases such as osteoporosis, for judging fracture risk, and for quantitatively diagnosing bone union after treatment of bone fracture.

The evaluation of bone formation and bone union depends largely on X-ray photography, but quantitatively diagnosing bone strength by means of X-ray photography is very difficult. As a related-art method of measuring bone strength, there is known a strength test of a sample bone of a measurement target. However, this method, which requires an extraction operation for obtaining a sample bone, is invasive. A method of measuring amount of bone and bone density has employed devices such as general-purpose X-ray CT and DXA (dual-energy X-ray absorptiometry) devices. However, these devices are merely means for measuring the amount of bone and cannot provide an evaluation of bone strength. Moreover, in light of the fact that tissue is irradiated with X-rays in these methods, these methods cannot be considered non-invasive.

Other attempts to quantitatively evaluate bone strength include a strain gauge method in which a strain gauge is mounted on an external fixator and the strain of the external fixator is measured; a vibration wave method in which a vibration is externally applied to a bone and a characteristic frequency is evaluated; and an acoustic emission method in which acoustic waves generated by a bone which has reached yield stress are detected. These methods, however, suffer from various problems, in that a limitation is imposed on the treatment to which these methods can be applied, that the bone is subjected to invasion, and that evaluation precision is insufficient.

In view of the above circumstances, the inventors of the present application have proposed an ultrasound diagnostic apparatus for noninvasively and quantitatively evaluating the mechanical characteristics of bone (refer to, for example, JP 2005-152079 A).

The ultrasound diagnostic apparatus described in JP 2005-152079 A forms a plurality of ultrasonic beams on a bone, obtains a plurality of echo signals corresponding to the individual ultrasonic beams to specify a surface point corresponding to the bone surface for each echo signal, and generates shape data of the bone surface on the basis of the plurality of surface points obtained from the plurality of echo signals. Then, a mechanical characteristic of the bone is evaluated on the basis of a change in the shape data when an external load is applied to the bone. Thus, the apparatus is an epoch-making technology capable of noninvasively and quantitatively evaluating the mechanical characteristics of a bone in a living organism from the shape data of the bone surface on the basis of the echo signals.

The inventors of the present application have further improved the epoch-making technology described in JP 2005-152079 A and have studied methods of evaluating the mechanical characteristic of hard tissue such as a bone with higher precision. In particular, the present inventors have continuously studied technologies for applying a load to hard tissue.

SUMMARY

The present invention was conceived in view of the above-described circumstances, and advantageously provides a technology for precisely applying a predetermined load to hard tissue.

In order to attain the above advantage, in accordance with an aspect of the present invention, there is provided a load apparatus which applies a load to hard tissue, comprising: a support member; an oscillation arm which moves in a seesaw fashion about an axis serving as a fulcrum, the axis being supported by the support member; a pressure mechanism which is provided on one side of the oscillation arm with respect to the fulcrum; and a balancer which is provided on the other side of the oscillation arm with respect to the fulcrum, wherein the pressure mechanism includes a pressurizer for applying to the hard tissue a load in accordance with a force supplied by a load weight, and an adjustment unit for adjusting a force to be applied to the pressurizer by the load weight.

BRIEF DESCRIPTION OF THE DRAWINGS

A preferred embodiment of the present invention will be described in detail by reference to the following figures, wherein.

DETAILED DESCRIPTION

A preferred embodiment of the present invention will be described in detail with reference to the accompanying drawings.

Figure 1:
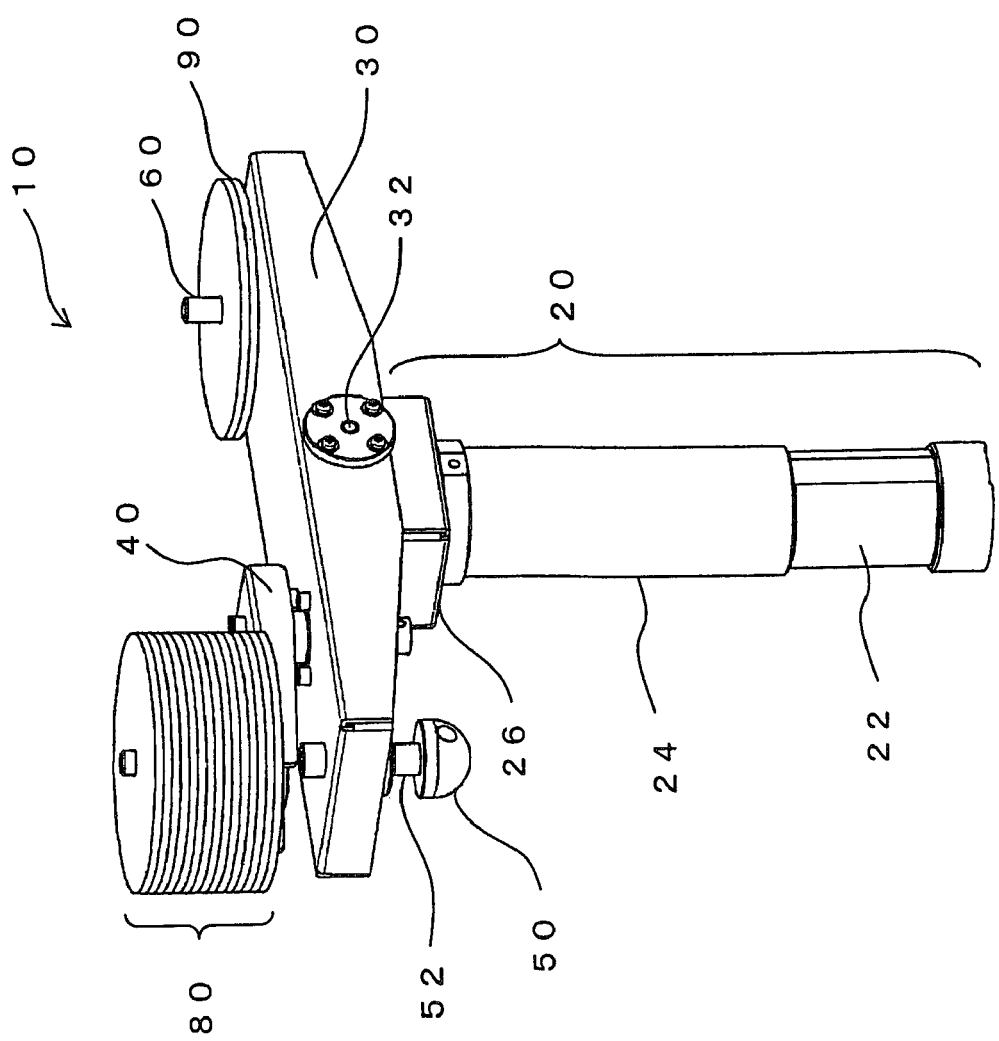
FIG. 1 is a perspective view showing the entire structure of a load apparatus according to an embodiment of the present invention.

FIG. 1 is a perspective view showing the entire structure of a preferred embodiment of a load apparatus according to the present invention. Referring to FIG. 1, a load apparatus 10 includes a support rod 20 which functions as a support member, and an oscillation arm 30 which moves in a seesaw fashion about an oscillation axis 32 which serves as a fulcrum and is supported by the support rod 20.

The support rod 20 is composed of an internal rod portion 22, an external cylinder portion 24, and an oscillation base 26. The internal rod portion 22 includes, at a bottom thereof, a magnet, which allows the load apparatus 10 to be secured with the support rod 20 standing upright on a base having a metallic plate, for example. The external cylinder portion 24 can move relative to the internal rod portion 22 along the longitudinal direction thereof. With this movement of the external cylinder portion 24, the height of the oscillation base 26 supporting the oscillation axis 32 is adjusted, which further results in adjustment of a pressurizing position of a pressurizer 50. The movement of the external cylinder portion 24; i.e., adjustment of the height, may be performed manually by a user or by means of a pump mechanism or the like which is provided within the support rod 20.

A rotation arm 40 and the pressurizer 50 are mounted on one end of the oscillation arm 30. One end of the rotation arm 40 is rotatably attached with respect to the oscillation arm 30, with a load weight 80 being placed on the other end of the rotation arm 40. By rotating the rotation arm 40, the magnitude of a force to be applied by the load weight 80 to the pressurizer 50 is adjusted. Here, a load cell 52 is attached to the pressurizer 50 for measuring the load to be applied by the pressurizer 50 to hard tissue such as a bone.

A support axis 60 for supporting an adjustment weight 90 is mounted on the other end of the oscillation arm 30. This adjustment weight 90 adjusts the weight balance between one side and the other side of the oscillation arm 30. The adjustment of the weight balance by the adjustment weight 90 and the adjustment of the magnitude of a force by the rotation arm 40 will be described in detail below.

Figure 2A:
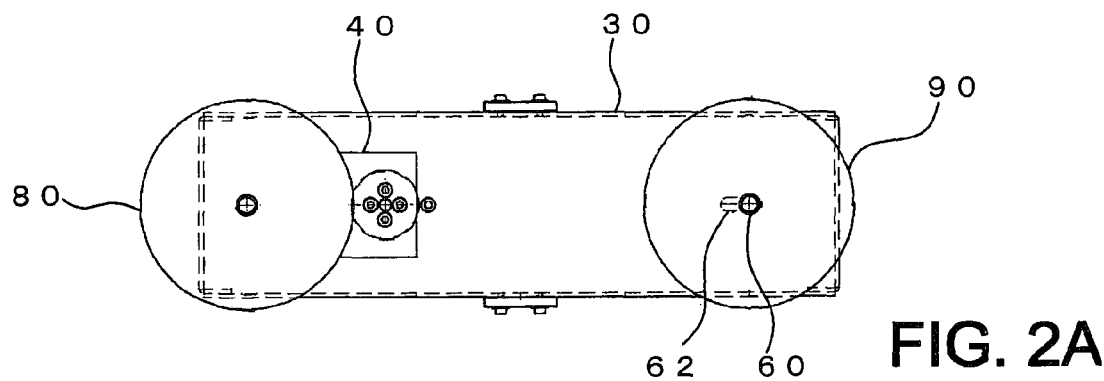
FIGS. 2A and 2B are a top view and a side view, respectively, of the load apparatus.
Figure 2B:
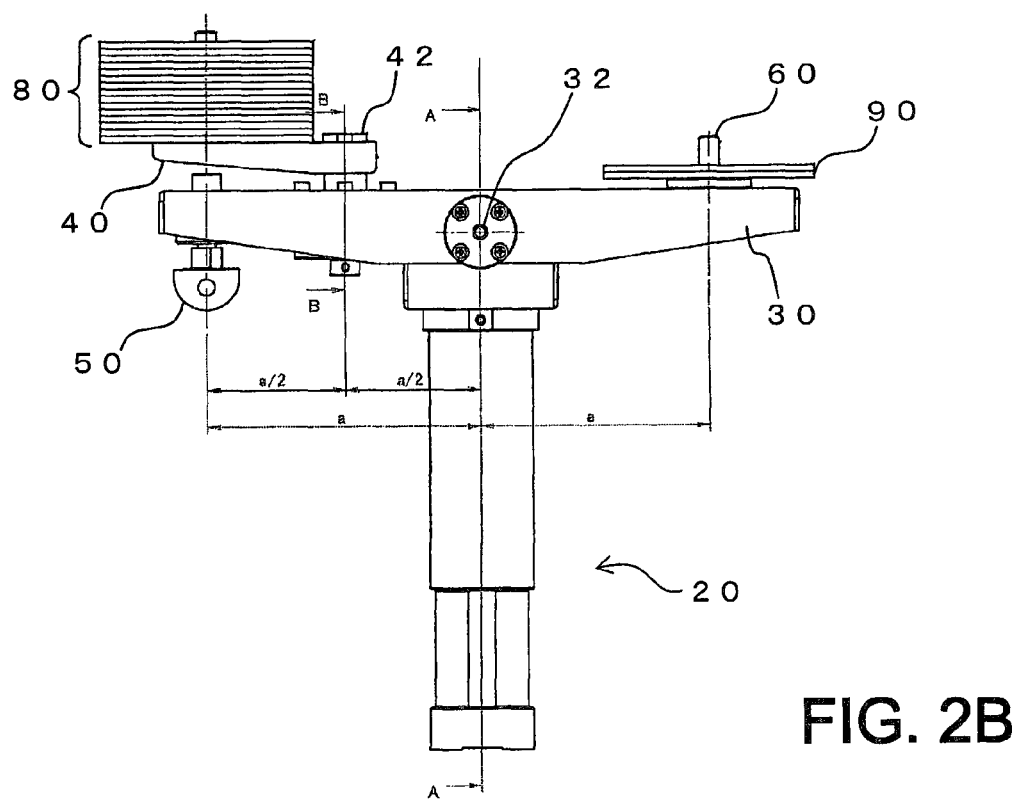

FIGS. 2A and 2B are a top view and a side view, respectively, of the load apparatus 10 shown in FIG. 1. As shown in FIG. 2B, assuming that the distance from the position where the pressurizer 50 of the oscillation arm 30 is provided to the position where the support axis 60 is provided is $2a$, the oscillation axis 32 is provided at the center point of the distance $2a$ in the longitudinal direction. Further, one end of the rotation arm 40 is attached to the oscillation arm 30 via a rotation axis 42 which is disposed at a position spaced from the oscillation axis 32 toward the one end of the oscillation arm 40 by a length of $a/2$. In addition, the pressurizer 50 is provided at a position which is spaced from the position of the rotation axis 42 by a distance of $a/2$ toward the one end of the oscillation arm 30. Further, in the example shown in FIG. 2B, the load weight 80 is located immediately above the pressurizer 50.

The rotation arm 40 rotates about the rotation axis 42. More specifically, the rotation arm 40 rotates within a plane including the upper surface of the oscillation arm 30 shown in FIG. 2A. When the rotation arm 40 rotates by 180 degrees from the state shown in FIG. 2, the load weight 80 which is placed on the other end of the rotation arm 40 moves to a position immediate above the oscillation axis 32. In this state, the magnitude of a force applied by the load weight 80 to the pressurizer 50 becomes 0.

The adjustment weight 90 is used to adjust the weight balance between the one end side and the other end side of the oscillation arm 30 in a state where the load weight 80 is displaced to a position immediately above the oscillation axis 32. Specifically, in a state in which the load weight 80 is displaced immediately above the oscillation axis 32, the weight of the adjustment weight 90 is appropriately adjusted such that the oscillation arm 30 and the support rod 20 are positioned orthogonal to each other. The adjustment weight 90 is formed of a plurality of disk-shape members, and the weight of the adjustment weight 90 as a whole is adjusted by changing the number of the disk-shape members, and so on. Further, the support axis 60 which supports the adjustment weight 90 can be displaced along a long hole 62 formed in the oscillation arm 30. As such, the adjustment weight 90 can be moved linearly along the longitudinal direction of the oscillation arm 30, to thereby fine-tune the weight balance.

Figure 3A:
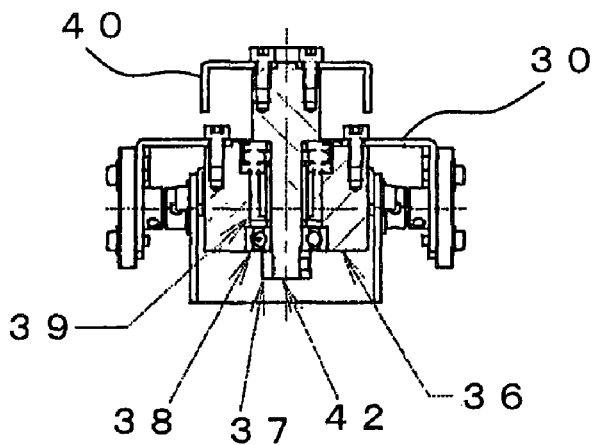
FIGS. 3A and 3B are cross sectional views of the load apparatus taken along lines A-A and B-B, respectively, of FIG. 2.
Figure 3B:
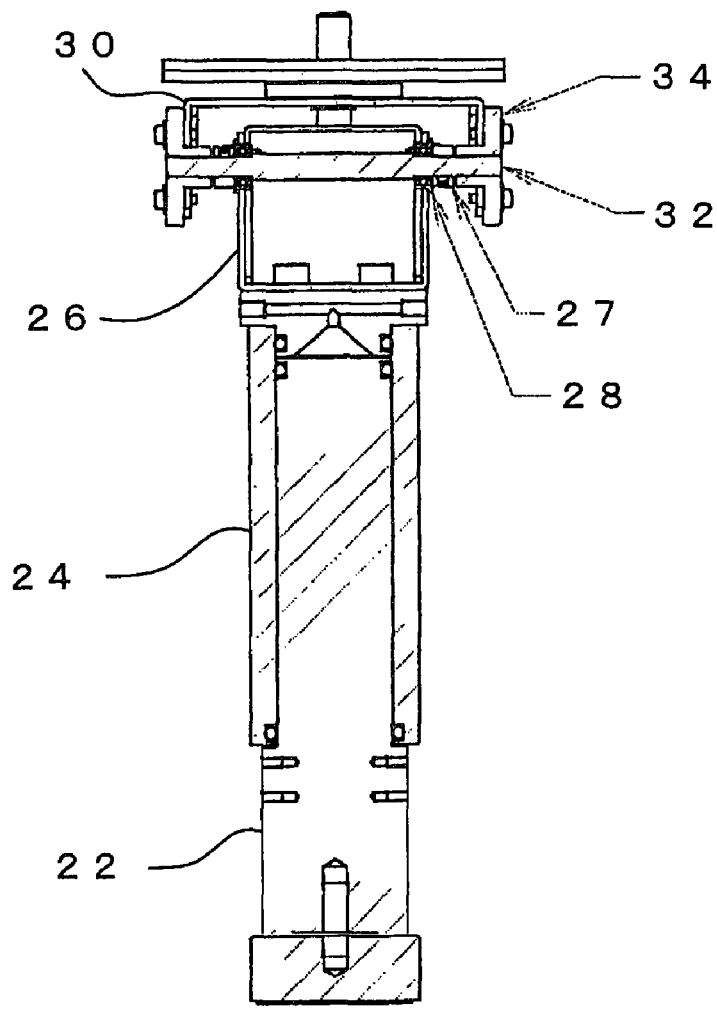

FIGS. 3A and 3B are cross sectional views taken along lines A-A and B-B, respectively, in FIG. 2B. Referring to FIG. 3B, the oscillation base 26 supports the oscillation axis 32 with a bearing 28, and a shift of the oscillation axis 32 in the axial direction is suppressed by a collar 27. The oscillation arm 30 is fixed in a fixation flange 34 and oscillates; i.e., moves in a seesaw fashion, about the oscillation axis 32.

Further, as shown in FIG. 3A, the rotation arm 40 is attached to the oscillation arm 30 via the rotation axis 42. The rotation axis 42 and the rotation arm 40 are fixed to each other. A bearing housing 36, the collar 37, a bearing 38, and a needle roller bearing with a thrust ball bearing 39 are mounted on the oscillation arm 30.

Figure 4A:
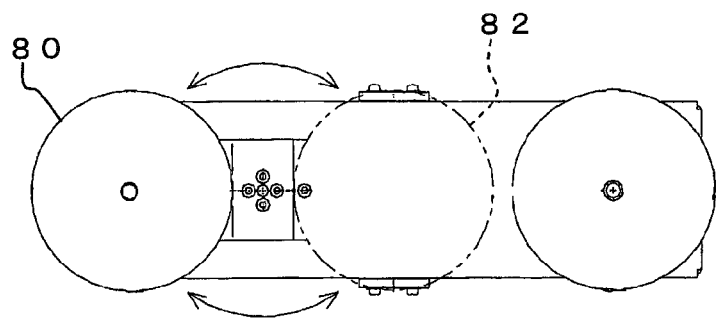
FIGS. 4A and 4B are views for explaining adjustment of a force generated by rotation of a rotating arm.
Figure 4B:
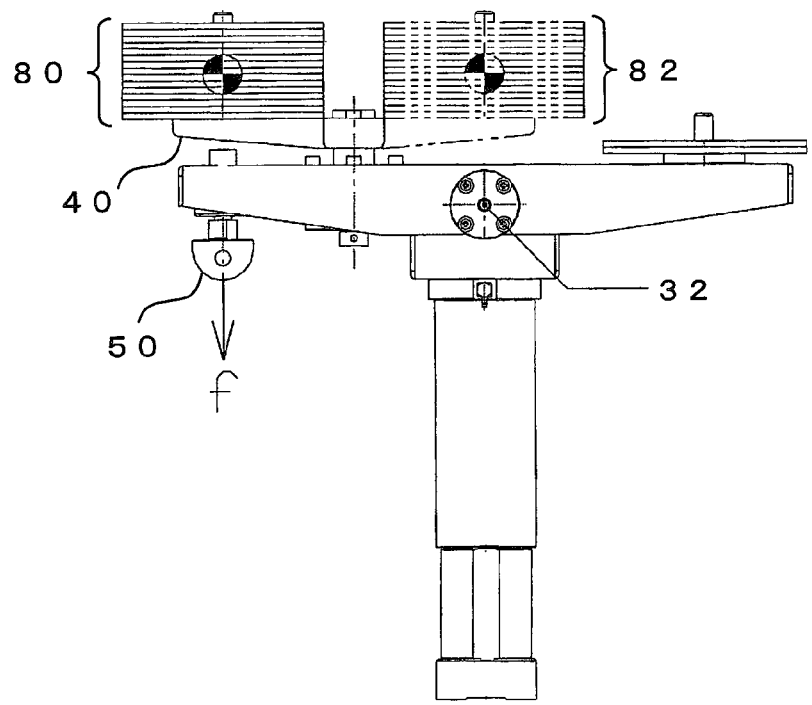

FIGS. 4A and 4B, which are a top view and a side view, respectively, of the load apparatus 10 shown in FIG. 1, are views for explaining adjustment of the magnitude of a force by means of rotation of the rotation arm 40. The load weight 80, in a state shown by a solid line in FIG. 4, is located immediately above the pressurizer 50. In this state, a force f which is to be applied to the pressurizer 50 by the load weight 80 is the maximum.

When the rotation arm 40 is rotated, the load weight 80 moves in the rotation direction indicated by arrows in FIG. 4A. By displacing the load weight 80 to a desired circumferential position, the magnitude of the force f can be changed. In particular, FIG. 4 shows a position 82 of the load weight 80 by a dotted line; that is, a state in which the load weight 80 is displaced to a position immediately above the oscillation axis 32. In this state, the force f which is to be applied to the pressurizer 50 by the load weight 80 is 0.

Here, the rotation arm 40 may be manually rotated by a user or may be rotated by using a motor or the like. Further, the load weight 80 is formed of a plurality of disk-shape members, and the weight of the load weight 80 as a whole is adjusted by changing the number of the disk-shape members, for example.

Figure 5:
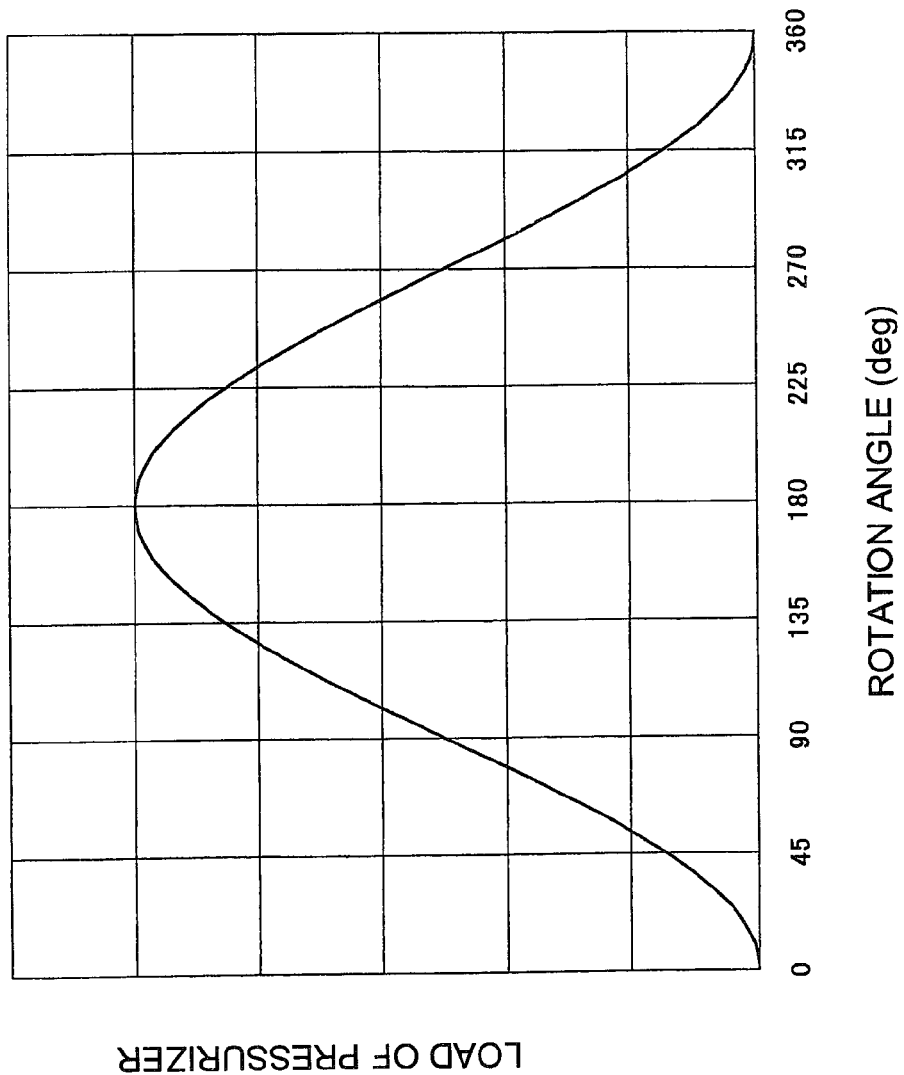
FIG. 5 is a view for explaining a relationship between a load applied by a pressurizer and a rotation angle of the rotating arm.

FIG. 5 is a view for explaining a relationship between the load to be applied to hard tissue by a pressurizer (compressor) and the rotation angle of the rotation arm. In FIG. 5, the horizontal axis indicates the rotation angle of the rotation arm and the vertical axis indicates the load of a pressurizer (compressor). Here, it is assumed that the rotation angle of the rotation arm when the load weight is located immediately above the oscillation axis (i.e. the position 82 shown in FIG. 4) is 0 degrees (0 deg).

With the rotation of the rotation arm in a predetermined direction from the state in which the rotation angle is 0 degrees, the load weight gradually approaches the pressurizer from the position immediately above the oscillation axis and therefore the load on the pressurizer gradually increases. Then, when the load weight reaches a position immediately above the pressurizer (i.e. the position of the load weight indicated by a solid line in FIG. 4); i.e., when the load weight is displaced to a position where the rotation angle is 180 degrees, the load of the pressurizer is maximized. When the rotation arm is further rotated in the predetermined direction, the load weight gradually approaches the oscillation axis and therefore the load on the pressurizer gradually decreases. Then, when the load weight returns to a position immediately above the oscillation axis; i.e., a position where the rotation angle is 360 degrees, the load on the pressurizer returns to a minimum (zero).

By displacing the load weight to a position along the circumference of a perfect circle by means of the rotation arm, loads having a sinusoidal waveform as shown in FIG. 5 can be generated. Further, by displacing the load weight by rotation to a predetermined position and stopping the load weight at this position, a static load corresponding to the rotation angle can be applied to the pressurizer.

Figure 6:
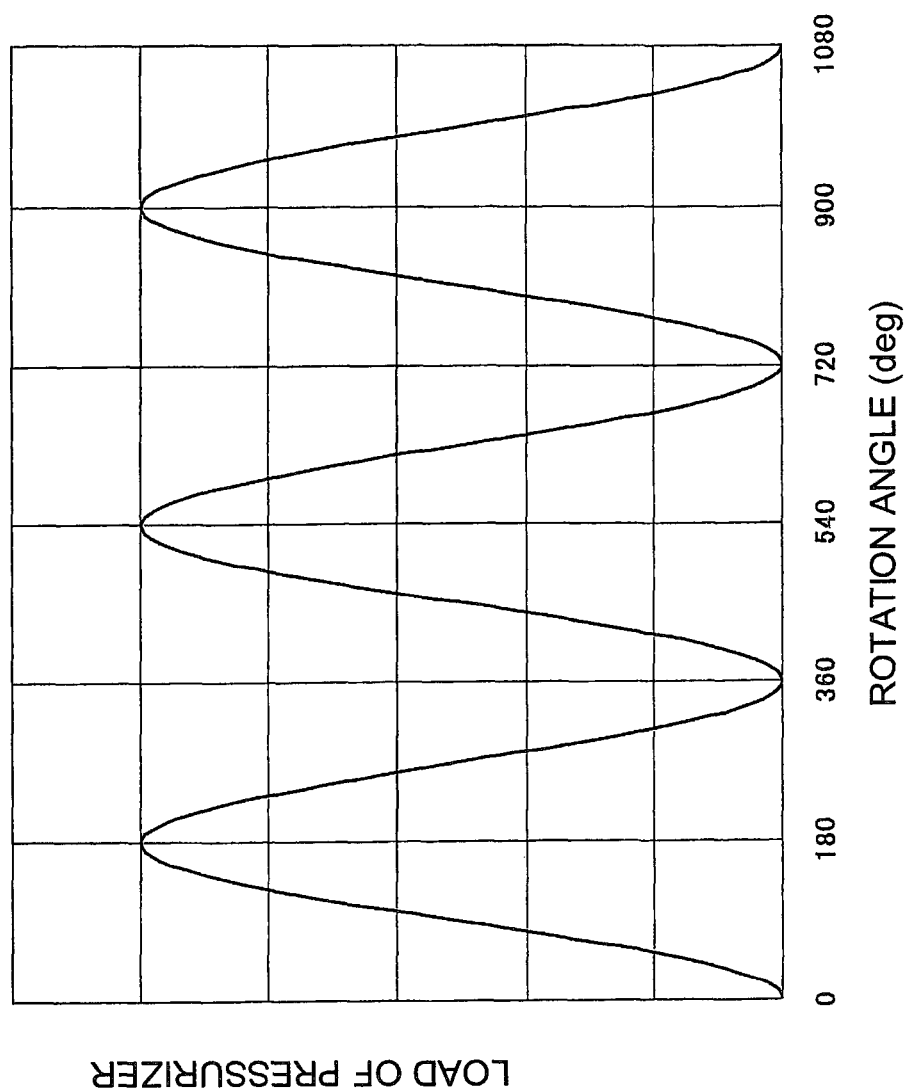
FIG. 6 is a view for explaining a change in the load with a continuous rotation movement.

FIG. 6 is a view for explaining a variation in the load on the pressurizer (compressor) when continuous rotational motion of the rotation arm is performed. In FIG. 6, the horizontal axis indicates the rotation angle of the rotation arm and the vertical axis indicates the load on the pressurizer (compressor). Here, similar to the example shown in FIG. 5, it is again assumed that the rotation angle of the rotation arm when the load weight is located immediately above the oscillation axis (i.e. the position 82 shown in FIG. 4) is 0 degrees (0 deg).

With the continuous rotational motion of the rotation arm in a predetermined direction, periodical loads having a sinusoidal waveform as shown in FIG. 6 can be generated. Specifically, by causing the load weight to perform rotational motion by means of the rotation arm, the magnitude of a force to be applied to the pressurizer varies in a periodic manner, so that a load which varies periodically can be applied to hard tissue.

Figure 7:
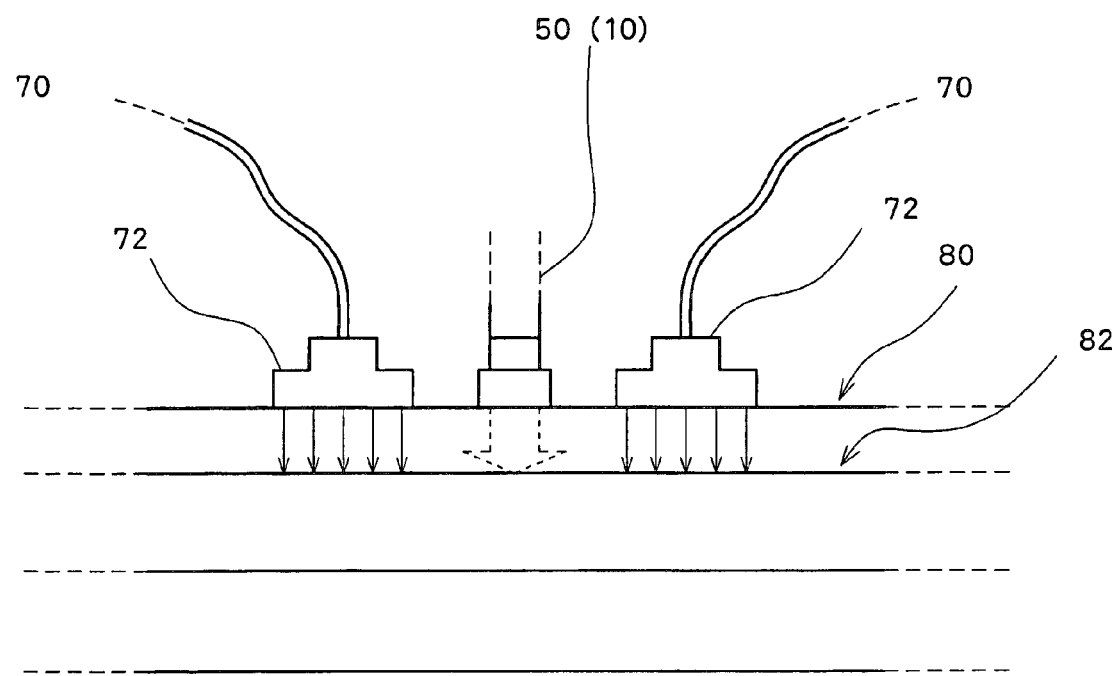
FIG. 7 is a view for explaining an ultrasound diagnosis apparatus provided with the load apparatus.

FIG. 7 is a view for explaining an ultrasound diagnostic system in which the load apparatus according to the present invention is employed. FIG. 7 shows a system in which an ultrasound diagnostic apparatus 70 is used for measuring a change in the shape of a bone 82 to which a load is applied by the load apparatus 10.

The load apparatus 10, which corresponds to the load apparatus 10 shown in FIG. 1, applies a load to the bone 82 of a subject 80 by means of the pressurizer. More specifically, with the rotation of the rotation arm, a force which is generated by the load weight and applied to the pressurizer 50 is adjusted, and a load is applied to the bone 82. Here, the bone to be diagnosed may be a tibia, fibula, etc.

The ultrasound diagnostic apparatus 70 forms a plurality of ultrasonic beams with respect to the bone 82 to which a load is to be applied by the load apparatus 10, and specifies a surface point on the bone 82 for each ultrasonic beam. Referring to FIG. 7, each of two probes 72 forms 5 ultrasonic beams. The ultrasound diagnostic apparatus 70 measures a change in the shape of the bone 82 caused by application of the load, based on the plurality of surface points obtained from the plurality of ultrasonic beams.

The ultrasound diagnostic apparatus 70 according to the present embodiment may be the apparatus described in JP 2005-152079 A, for example. More specifically, the probe 72, which is an ultrasonic probe, is brought into contact with a body surface of the subject 80 to form a plurality of ultrasonic beams toward the bone 82 in the body of the subject 80. Echo signals obtained through the probe 72 are processed in the main body of the ultrasound diagnostic apparatus which is not shown. For example, with echo tracking processing, a surface of the bone is detected with regard to each ultrasonic beam, and a shape change of the bone 82; e.g., an angle change of the bone surface, which is described in detail in JP 2005-152079 A, is measured based on a displacement of the surface.

As described above with reference to FIG. 5, according to the load apparatus 10 of the present embodiment, by displacing the load weight to a predetermined position by rotation and stopping the load weight at this position, a static load corresponding to the rotation angle can be applied to the pressurizer. In the present system, a change in the shape of the bone 82 caused by application of such a load is measured by the ultrasound diagnostic apparatus 70. Consequently, elasticity of the bone 82 can be assessed based on the relationship between the amount of load applied to the bone 82 and the amount of change in the shape of the bone 82. For example, there is measured a change in the shape of the bone 82 which is caused by applying a predetermined amount of load for a predetermined time period.

The operations for measuring the elasticity are performed in the following procedure, for example. First, a load weight which is equal to the load to be applied to the subject (bone 82) is placed on the rotation arm of the load apparatus 10.

Then, the rotation arm is rotated to move the load weight to the position of the fulcrum (i.e. immediately above the oscillation axis). Further, the pressurizer 50 of the load apparatus 10 is placed on the subject 80, and, in this state, the length (height) of the support rod is adjusted such that the oscillation arm is kept level. Next, the rotation arm is rotated to displace the load weight to a position immediately above the pressurizer 50, which then applies a predetermined amount of static load to the bone 82. A change in the shape of the bone 82 caused by application of the load in this state is then measured by the ultrasound diagnostic apparatus 70. When the measurement is completed, the rotation arm of the load apparatus is rotated to move the load weight back to the position of the fulcrum, where the load on the bone 82 is released.

Further, as described above with reference to FIG. 6, with the load apparatus 10 of the present embodiment, the load weight is caused to perform rotational motion by means of the rotation arm to thereby periodically change the magnitude of the force to be applied to the pressurizer 50, so that a load which varies periodically can be applied to the bone 82. In the present system, a change in the shape of the bone 82 caused by application of such a load is measured by the ultrasound diagnostic apparatus 70. Consequently, based on followability (a degree of follow) of the shape change in the bone 82 with respect to the periodical load applied to the bone 82, viscoelasticity of the bone 82 can be assessed. For example, the followability of the shape change in the bone 82 caused by application of the periodically changing load as shown in FIG. 6 is measured.

The operations for measuring the viscoelasticity are performed in the following procedure, for example. First, a load weight which is equal to the load to be applied to the subject (bone 82) is placed on the rotation arm of the load apparatus 10. Then, the rotation arm is rotated to move the load weight to the position of the fulcrum (i.e. immediately above the oscillation axis). Further, the pressurizer 50 of the load apparatus 10 is placed on the subject 80, and, in this state, the length (height) of the support rod is adjusted such that the oscillation arm is kept level. Next, the rotation arm is continuously rotated to cause the load weight to perform a uniform circular motion along the circumference, to thereby apply a periodical load having a sinusoidal waveform to the bone 82. The followability of the change in the shape of the bone 82 caused by application of the load in this state is then measured by the ultrasound diagnostic apparatus 70. When the measurement is completed, the rotation arm of the load apparatus is rotated to move the load weight back to the position of the fulcrum, where the load on the bone 82 is released.

A preferred embodiment of the present invention has been described. According to the present embodiment, as the oscillation arm oscillates by means of the weight of the load weight to thereby apply a load to the subject, even when the subject moves, the oscillation arm follows the movement to thereby continue to apply an accurate load to the subject. Further, because there can be prevented application of a load exceeding the load weight and the self weight of the apparatus in the vicinity of the pressurizer, the load apparatus of the present embodiment is excellent in terms of safety. Also, because the weight of the load weight can be visually recognized, advantages of preventing application of excess loads can be expected.

Although the preferred embodiment of the present invention has been described using specific terms, such description is for illustrative purposes only, and it is to be understood that changes and variations may be made without departing from the spirit or scope of the appended claims.

What is claimed is:

1. A load apparatus which applies a load to hard tissue, comprising:
   a support member;
   an oscillation arm which moves in a seesaw fashion about an axis serving as a fulcrum, the axis being supported by the support member;
   a pressure mechanism which is provided on one side of the oscillation arm with respect to the fulcrum; and
   a balancer which is provided on the other side of the oscillation arm with respect to the fulcrum,
   wherein
   the pressure mechanism includes:
   a load weight disposed on the one side of the oscillation arm with respect to the fulcrum;
   a pressurizer for applying to the hard tissue a load corresponding to a force supplied by the load weight; and
   an adjustment unit disposed on the one side of the oscillation arm with respect to the fulcrum, wherein the adjustment unit rotates the load weight to adjust a magnitude of the force to be applied to the pressurizer by the load weight.

2. The load apparatus according to claim 1, wherein the adjustment unit includes a rotation arm for rotating the load weight, one side of the rotation arm being rotatably attached to the oscillation arm, and the load weight being attached to the other side of the rotation arm.

3. The load apparatus according to claim 2, wherein the balancer adjusts weight balance between one side and the other side of the oscillation arm in a state in which the load weight is moved by the rotation arm to a position immediately above the fulcrum.

4. The load apparatus according to claim 3, wherein the balancer moves an adjustment weight linearly along the longitudinal direction of the oscillation arm to fine-tune the weight balance.

5. The load apparatus according to claim 2, wherein the rotation arm causes the load weight to perform rotational motion to allow periodic variation of the magnitude of a force to be applied to the pressurizer, for applying to the hard tissue a load which varies periodically.

6. The load apparatus according to claim 5, wherein the rotation arm rotates about an axis which is attached to the oscillation arm on one side of the rotation arm, to cause the load weight which is attached on the other side of the rotation arm to perform rotational motion between the position immediately above the fulcrum and a position immediately above the pressurizer.

7. The load apparatus according to claim 6, wherein the rotation arm moves the load weight along a circumference of a perfect circle to allow application to the hard tissue of a periodical load having a sinusoidal waveform.

8. The load apparatus according to claim 7, wherein the balancer adjusts weight balance between one side and the other side of the oscillation arm in a state in which the load weight is moved by the rotation arm to a position immediately above the fulcrum.

9. The load apparatus according to claim 8, wherein the balancer moves an adjustment weight linearly along the longitudinal direction of the oscillation arm to fine-tune the weight balance.

10. The load apparatus according to claim 2, wherein the rotation arm displaces the load weight by rotation to a predetermined position to allow application to the pressurizer of a force of a predetermined magnitude for applying a predetermined amount of static load to the hard tissue.

11. The load apparatus according to claim 10, wherein the rotation arm rotates about an axis which is attached to the oscillation arm on one side of the rotation arm, to displace the load weight which is attached on the other side of the rotation arm by rotation between the position immediately above the fulcrum and a position immediately above the pressurizer.

12. The load apparatus according to claim 11, wherein the balancer adjusts weight balance between one side and the other side of the oscillation arm in a state in which the load weight is moved by the rotation arm to a position immediately above the fulcrum.

13. The load apparatus according to claim 12, wherein the balancer moves an adjustment weight linearly along the longitudinal direction of the oscillation arm to fine-tune the weight balance.

* * * * *